United States Patent [19]

Beck et al.

[11] 4,048,202

[45] Sept. 13, 1977

[54] 3-O-ALKANOYLGLYCERIC ACIDS

[75] Inventors: Charles I. Beck, Skokie; Roger M. Layton, Buffalo Grove, both of Ill.

[73] Assignee: G. D. Searle & Co., Chicago, Ill.

[21] Appl. No.: 567,400

[22] Filed: Apr. 11, 1975

[51] Int. Cl.$^2$ .................. C11C 3/02; C07C 69/02
[52] U.S. Cl. ............... 260/410.6; 260/486 R; 424/312; 560/263
[58] Field of Search ............. 260/404, 410.6, 410.7, 260/488 J; 424/312

[56] References Cited

U.S. PATENT DOCUMENTS 3,551,464  12/1970  Miller .................. 260/410.6

OTHER PUBLICATIONS

Markley, K., Fatty Acids, 2nd Ed., Pt. 2 (1961) pp. 808–811.
Bull. Soc. Chim. Biol. Fr., 52(2), 211–227 (1976).
Noller, Chemistry of Organic Compounds, 3rd. ed., 1965, pp. 189–190.

*Primary Examiner*—Patrick P. Garvin
*Assistant Examiner*—John F. Niebling
*Attorney, Agent, or Firm*—John J. McDonnell

[57] ABSTRACT

3-O-Alkanoylglyceric acids and their salts having antimicrobial properties are described herein. These compounds also have useful surfactant properties. The subject compounds can be prepared by reacting the appropriate acid chloride with glyceric acid.

7 Claims, No Drawings

3-O-ALKANOYLGLYCERIC ACIDS

The present invention relates to a group of 3-O-alkanoylglyceric acids. More particularly, the present invention relates to a group of compounds having the general formula $$R-\overset{O}{\underset{\|}{C}}-OCH_2 \\ \phantom{R-C-O}| \\ \phantom{R-C-O}CHOH \\ \phantom{R-C-O}| \\ \phantom{R-C-O}COOH \qquad (I)$$

wherein R is straight or branched chain alkyl having from 1 to 20 carbon atoms, or alkenyl having from 10 to 20 carbon atoms, and the corresponding non-toxic pharmaceutically acceptable salts thereof.

The alkyl radicals referred to above are exemplified by radicals such as methyl, ethyl, n-butyl, isobutyl, n-pentyl, n-hexyl, n-heptyl, n-nonyl, n-decyl, pentadecyl, heptadecyl, and like alkyl radicals of the formula $$C_nH_{2n+1}$$

wherein $n$ is 1 to 20.

The alkenyl radicals referred to above are represented by radicals such as cis-7-pentadecenyl, cis-8-heptadecenyl, cis,cis-6,9-heptadecadienyl and cis,cis,cis-3,6,9-heptadecatrienyl.

Equivalent to the compounds of formula (I) for the purpose of this invention are the alkali metal, alkaline-earth metal, and ammonium salts thereof. These salts are preparable by contacting with one equivalent of lithium, sodium, potassium, barium, strontium, calcium, ammonium, or like hydroxide in an aqueous medium.

Especially preferred compounds are those wherein R is a n-pentyl, n-nonyl, n-dodecanyl or a n-pentadecanyl radical, and their corresponding non-toxic pharmaceutically acceptable salts.

3-O-benzoyloxyglyceric acid is described in Bull. Soc. Chim. Biol. Fr., 52(2), 211-27 (1970). The compounds of the present invention are particularly distinct, having an alkanoyl moiety instead of benzoyloxy.

The compounds to which this invention relates are useful by reason of their valuable biological and physical chemical properties. In particular, they possess activity as anti-microbial agents. Thus, they inhibit or prevent the growth of bacteria such as Clostridium paraputrificum, Clostridium botulinum, Clostridium perfingens, and Bacillus subtilis.

The utility of the present compounds in respect of Clostridium botulinum can be demonstrated by the following test procedure.

Fluid thioglycollate medium (manufactured by Baltimore Biological Laboratories or Difco) is prepared as recommended by the manufacturer, adjusted to a pH of 5 (or left at a pH of 7), sterilized, and inoculated with C. botulinum (ATCC 19397)* q.s. one million cells per ml., determined spectrophotometrically. Meanwhile, the compound is heated in sterile distilled water at a concentration of 100000 μg. per ml. at a temperature of 80° C. for 20 minutes. This compound preparation is serially diluted and mixed with sufficient inoculated medium to afford concentrations of 10000, 1000, 100 and 10 μg. of compound per ml. The mixtures thus obtained are incubated anaerobically for 20 to 24 hours at 37° C. and then examined grossly for growth of the organism. Controls are provided by concurrent incubations identical with the above except that the test compound is omitted. Compounds are considered active if, at the maximum concentrations tested, no growth of organism is observed and no aberrance is apparent in respect of the controls. Potency is expressed as the minimum concentration at which a compound is active.

[*ATCC refers to American Type Culture Collection located at 12301 Parklawn Drive, Rockville, Maryland 20852.]

When the C. botulinum of the above procedure is substituted by C. perfingens (ATCC 13124), C. perfingens (ATCC 1620-19) or C. paraputrificum (ATCC 1620-23), and the test procedure repeated, the present compounds display further antibacterial activity. The utility of the present compounds can also be demonstrated in respect of B. subtilis in the standardized test described in U.S. Pat. No. 3,668,251.

The results of these standardized tests are illustrated in Table 1.

Table 1

| Organism | Minimum Inhibitory Concentrations (μg/ml) | | | | | | | |
|---|---|---|---|---|---|---|---|---|
| | *R=5 | | *R=9 | | *R=12 | | *R=15 | |
| | pH 5 | pH 7 | pH 5 | pH 7 | pH 5 | pH 7 | pH 5 | pH 7 |
| C.botulinum (ATCC 19397) | 10 | 100 | 10 | 10 | 10 | 100 | 100 | 1000 |
| C.perfingens (ATCC 13124) | 100 | 1000 | 10 | 10 | 10 | 100 | 10 | 1000 |
| C.perfingens (ATCC 1620-19) | 10 | 1000 | 10 | 100 | 10 | 10 | 100 | 100 |
| C.paraputrificum | 10 | 1000 | 10 | 100 | 10 | 100 | 10 | 1000 |
| B.subtilis | 10 | 10000 | 10 | 1000 | 10 | 1000 | >10000 | 10000 |

*R refers to the number of carbon atoms in the R moiety of formula 1.

Those skilled in the art will recognize that observations of activity in standardized tests for particular biological effects are fundamental to the development of valuable new drugs, both veterinary and human.

Compounds of the present invention also have useful surfactant properties and are thus useful as antimicrobials, as surfactants such as emulsifiers, and as dual functional agents.

The compounds of the present invention can be conveniently prepared by contacting glyceric acid with the appropriate acid chloride as shown in the following scheme:

$$R-\overset{O}{\underset{\|}{C}}-Cl + \begin{array}{c} H-OCH_2 \\ | \\ CHOH \\ | \\ COOH \end{array} \longrightarrow R-\overset{O}{\underset{\|}{C}}-O-CH_2 \\ \phantom{R-C-O-}| \\ \phantom{R-C-O-}CHOH \\ \phantom{R-C-O-}| \\ \phantom{R-C-O-}COOH$$

wherein R is defined as before. This reaction is conducted in a suitable solvent such as pyridine.

In the above indicated manner decanoyl chloride is reacted with glyceric acid in pyridine to provide 3-O-decanoylglyceric acid.

Time and temperature are not critical factors. The reaction is typically conducted at room temperature. Time varies from a few hours to several days, depending on the particular temperature employed.

The invention will appear more fully from the examples which follow. These examples are given by way of illustration only and are not to be construed as limiting the invention either in spirit or scope as many modifications both in materials and methods wils be apparent to those skilled in the art. In these examples, temperatures are given in degrees Centigrade (° C.) and quantities of materials are expressed in parts by weight unless otherwise specified. The relationship between parts by weight and parts by volume is the same as that existing between grams and milliliters.

EXAMPLE 1

A slurry of 6.4 parts of calcium glycerate dihydrate and 10 parts of water is acidified with vigorous stirring to a pH of 2.0 with a 30% solution of sulfuric acid. The viscosity of the slurry decreases rapidly with the addition of acid because glyceric acid is generated and concommitantly calcium sulfate precipitates. The precipitate is filtered from the solution; 137 parts of pyridine is added, and distillation of the water-pyridine 43:57 azeotrope at about 93° C. is begun. The distillation is continued, with the addition of freshly dried pyridine to retain pot volume, until the temperature rises to about 115° C. and the water content is substantially exhausted. There is thus obtained a solution of glyceric acid in pyridine.

To the above solution is added incrementally over a 20 minute period, 8.6 parts of decanoyl chloride. The reaction is stirred for 48 hours, and then quenched by adding ice water. After adjusting the pH to 2.5 with a 10% solution of sulfuric acid, the solution is extracted with methylene chloride. The organic phase is then separated, washed twice with water and once with a saturated sodium chloride solution. The solvent is removed in vacuo, leaving crude 3-O-decanoylglyceric acid as a straw yellow oil. Recrystallization from hexane provides pure 3-O-decanoylglyceric acid, melting at 67°-69° C., as snow white crystals. This product is represented by the following structural formula:

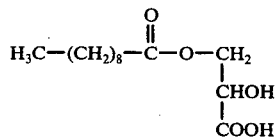

EXAMPLE 2

Substitution of an equivalent quantity of hexanoyl chloride, tridecanoyl chloride or hexadecanoyl chloride for the decanoyl chloride used in Example I and substantial repetition of the procedure detailed in the second paragraph of that example affords 3-O-hexanoyl-glyceric acid, 3-O-tridecanoylglyceric acid and 3-O-hexadecanoylglyceric acid, respectively. These compounds are represented by the following structural formulas:

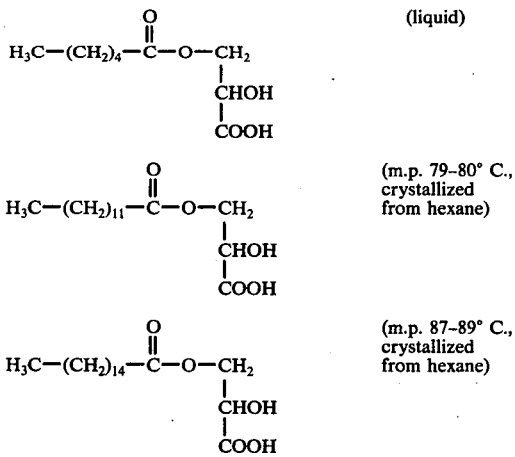

EXAMPLE 3

When equivalent quantities of cis-9-octadecenoyl chloride (oleoyl chloride) or cis,cis-9,12-octadecadienoyl chloride (linoleoyl chloride) are substituted for the decanoyl chloride of Example I, and the procedure detailed therein substantially repeated, there is obtained 3-O-cis-9-octadecanoylglyceric acid (3-O-oleoylglyceric acid) and 3-O-cis,cis-9,12-octadecadienoylglyceric acid (3-O-linoleoylglyceric acid), respectively.

What is claimed is:

1. A compound of the formula

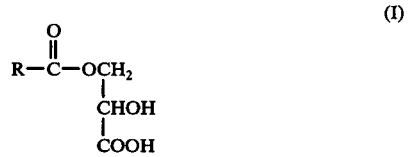

wherein R is alkyl having from 1 to 20 carbon atoms, or alkenyl having from 10 to 20 carbon atoms, and the corresponding non-toxic pharmaceutically acceptable salts thereof.

2. The compound according to claim 1 which is 3-O-hexanoylglyceric acid.

3. The compound according to claim 1 which is 3-O-decanoylglyceric acid.

4. The compound according to claim 1 which is 3-O-tridecanoylglyceric acid.

5. The compound according to claim 1 which is 3-O-hexadecanoylglyceric acid.

6. The compound according to claim 1 which is 3-O-cis-9-octadecenoylglyceric acid.

7. The compound according to claim 1 which is 3-O-cis,cis-9,12-octadecadienoylglyceric acid.

* * * * *